United States Patent
Thomas et al.

(10) Patent No.: US 6,852,996 B2
(45) Date of Patent: Feb. 8, 2005

(54) ORGANIC SEMICONDUCTOR SENSOR DEVICE

(75) Inventors: Danielle A. Thomas, Montbonnot (FR); Bruno J. Debeurre, Phoenix, AZ (US); Peter J. Thoma, Dallas, TX (US)

(73) Assignee: STMicroelectronics, Inc., Carrollton, TX (US)

( * ) Notice: Subject to any disclaimer, the term of this patent is extended or adjusted under 35 U.S.C. 154(b) by 118 days.

(21) Appl. No.: 10/254,311

(22) Filed: Sep. 25, 2002

(65) Prior Publication Data

US 2004/0056245 A1 Mar. 25, 2004

(51) Int. Cl.⁷ .............................................. H01L 35/24
(52) U.S. Cl. ........................ 257/40; 257/252; 257/414
(58) Field of Search ......................... 257/40, 252, 253, 257/414; 324/686

(56) References Cited

U.S. PATENT DOCUMENTS

| | | | |
|---|---|---|---|
| 4,222,903 A | | 9/1980 | Heeger et al. |
| 4,353,056 A | | 10/1982 | Tsikos |
| 4,550,221 A | | 10/1985 | Mabusth |
| 5,981,970 A | | 11/1999 | Dimitrakopoulos |
| 6,114,862 A | * | 9/2000 | Tartagni et al. ............. 324/662 |
| 6,252,245 B1 | | 6/2001 | Katz et al. |
| 6,278,127 B1 | | 8/2001 | Dodabalapur et al. |
| 6,326,640 B1 | * | 12/2001 | Shi et al. ....................... 257/40 |
| 2003/0092208 A1 | * | 5/2003 | Trezza et al. .................. 438/22 |
| 2004/0099065 A1 | * | 5/2004 | Deconde et al. ........ 73/862.046 |

* cited by examiner

*Primary Examiner*—Tom Thomas
*Assistant Examiner*—Matthew Landau
(74) *Attorney, Agent, or Firm*—Lisa K. Jorgenson; Peter J. Thoma

(57) ABSTRACT

Sensor cells are arranged in an array in an organic semiconductor layer. Row and column select circuitry addresses the cells of the array one cell at a time to determine the presence of an object, such as a fingerprint ridge or valley, contacting or proximate to a sensing surface above each cell. Control circuitry can be provided in a companion silicon chip or in a second layer of organic semiconductor material to communicate with the array and an associated system processor. The array of sensor cells can be fabricated using a flexible polymer substrate that is peeled off and disposed of after contacts have been patterned on the organic semiconductor layer. The organic semiconductor layer can be used with a superimposed reactive interface layer to detect specific chemical substances in a test medium.

8 Claims, 7 Drawing Sheets

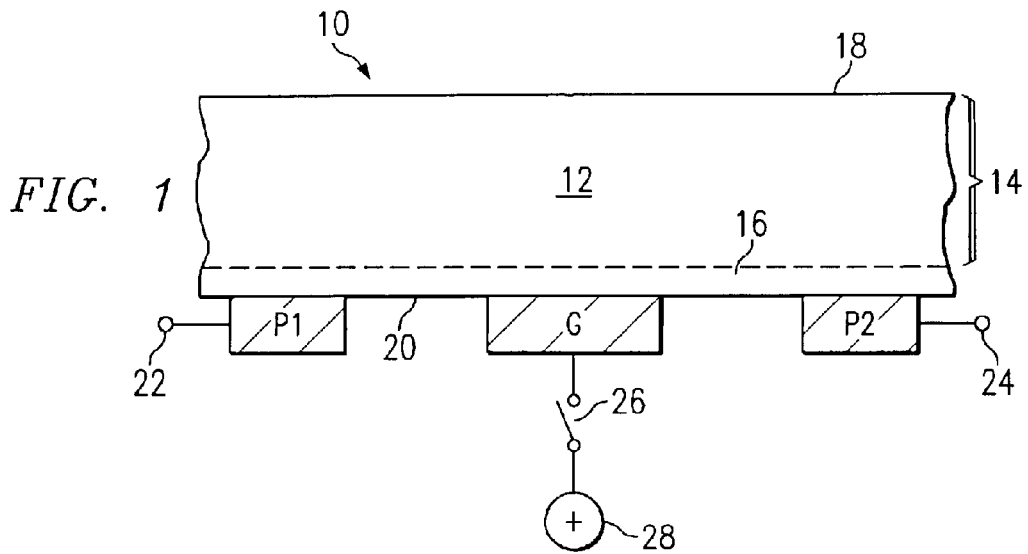
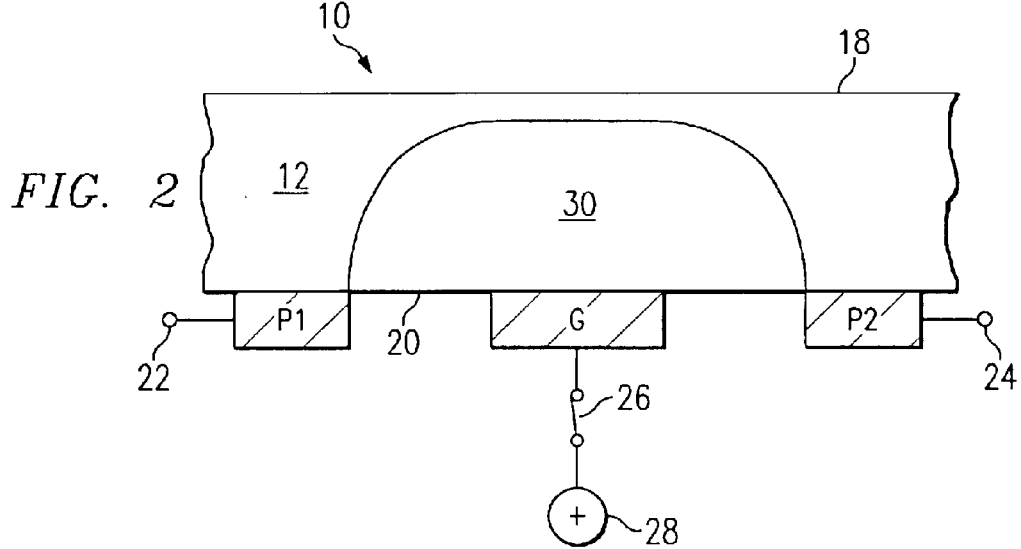
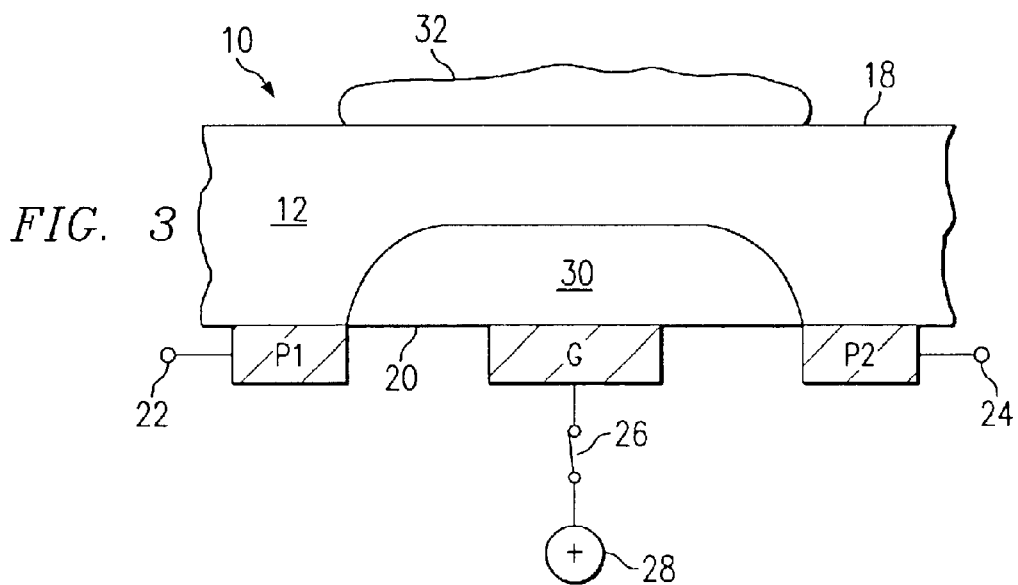

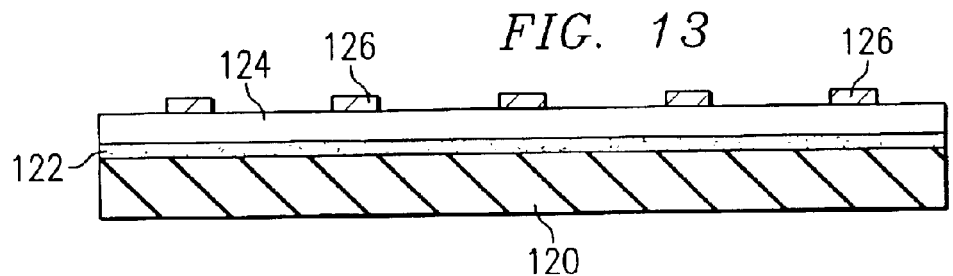
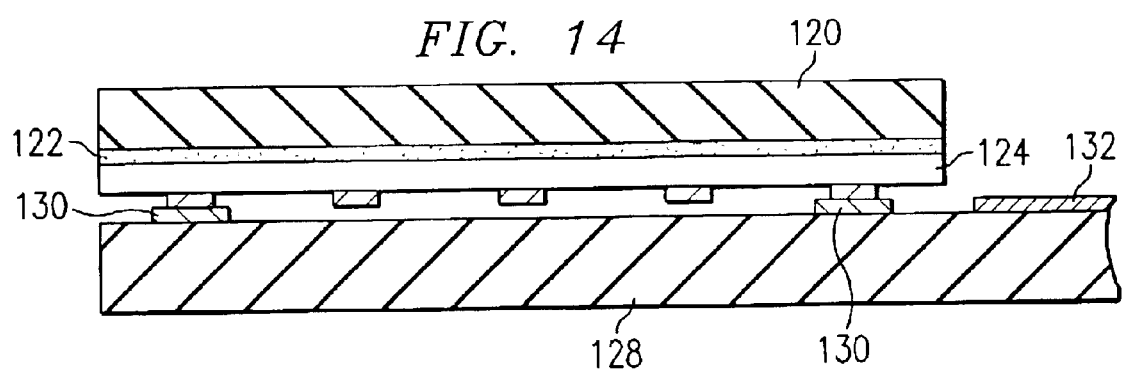
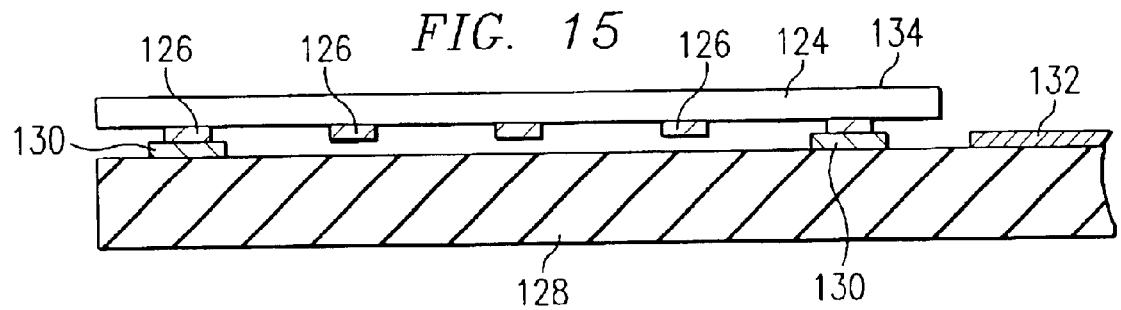

ORGANIC SEMICONDUCTOR SENSOR DEVICE

BACKGROUND OF THE INVENTION

The present invention relates generally to devices and methods of device fabrication using organic semiconductor materials, and more particularly to sensor devices having an organic semiconductor layer that performs a sensing function.

It is well known that organic polymeric materials can have compositions that produce mobile charge carriers, enabling the manufacture of organic semiconductor devices. U.S. Pat. No. 4,222,903 discloses a p-type conductivity polyacetylene film that can be doped with acceptor dopants to selectively increase its p-type electrical conductivity. A semiconductor material is known as "p-type" conductivity when its majority mobile charge carriers are positive charge carriers called "holes." A semiconductor material is known as "n-type" conductivity when its majority mobile charge carriers are negative charge carriers or "electrons."

Inorganic semiconductor materials, principally monolithic crystalline silicon, are readily fabricated so that both n-type and p-type regions can be formed in a silicon chip. Additionally, inorganic semiconductor materials have much higher charge carrier mobilities than organic semiconductor materials. Such characteristics enable silicon semiconductor devices to dominate high speed, high density semiconductor applications using various microscopic elements, like MOSFETs, constructed from n-type and p-type regions in a silicon chip. Yet, organic semiconductor materials have advantages over silicon in their relative simplicity of fabrication and lower finished-device cost. Organic semiconductor materials also have certain functional advantages over silicon-based devices. For example, organic semiconductor devices do not require the same rigid, hermetically sealed packages that are commonly employed with silicon semiconductor devices, since organic semiconductor devices are less susceptible to damage from exposure to various contaminants.

However, as observed in U.S. Pat. No. 6,252,245, only a limited number of organic semiconductor materials have been developed that are n-type. This has restricted the functionality of organic semiconductor devices and limited their practical applications. The fused-ring tetracarboxylic diimide compounds disclosed in U.S. Pat. No. 6,252,245 have the potential to enable practical fabrication of both n-channel and p-channel organic thin film transistors (OTFTs), from which complementary OTFT circuits can be constructed. Devices made using such or similar organic semiconductor technologies can incorporate complex circuit functionality enabling practical applications that do not require the circuit densities and high switching speeds of present silicon-based semiconductor devices.

Additionally, certain applications of organic semiconductor technology may require only p-type material for the fabrication of practical devices. Since the decades old work done with materials like polyacetylene, described for example in U.S. Pat. No. 4,222,903, higher performance p-type materials have been disclosed in the art. As an example, U.S. Pat. No. 5,981,970 discloses the use of pentacene to manufacture a p-type OTFT with a relatively high field-effect mobility.

The above-noted U.S. Pat. Nos. 4,222,903; 5,981,970; and 6,252,245 are hereby incorporated by reference. These patents are only a few representative examples of an extensive body of knowledge that has arisen in recent years in the field of organic semiconductor materials. It would be desirable to employ organic semiconductor technology in the design of sensor devices for reasons that will become apparent from the following description of the invention.

SUMMARY OF THE INVENTION

A principal object of the present invention is to provide a sensor device fabricated using organic semiconductor material. The sensor device may have a single sensor element or an array of sensor cells formed in a layer of organic semiconductor material. The layer may have a sensing surface on one side and contacts on the opposite side. Means are provided for communicating with the contacts to determine a condition sensed by the sensor element or the conditions sensed by each of the multiple sensor cells in an array.

In a preferred implementation, the present invention provides an organic semiconductor sensor device in which a sensor element has a capacitance that varies with the dimensions of a depletion region. The capacitance may vary in response to an object that may be on or proximate to a sensing surface of the sensor element, thereby modulating the depletion region.

In the application in which the sensor element is one of many such elements or cells arranged in an array, circuitry is included for selecting one sensor cell of the array at a time, sensing the capacitance value of the selected sensor cell, and communicating the capacitance value to a system processor. The system processor receives capacitance values for all of the sensor cells of the array in a timed sequence and processes the capacitance value data to determine characteristics of the object being sensed. This application is ideally suited for use in a fingerprint detector.

In a preferred method of fabrication, an organic semiconductor layer is formed over a flexible polymer substrate. A peelable film is provided on the top surface of the substrate that supports the organic semiconductor layer. Contacts are patterned on the exposed surface of the organic semiconductor layer, which is then inverted and mounted on a second permanent substrate. The flexible polymer substrate is then peeled off and disposed of leaving a sensing surface of the organic semiconductor layer exposed.

In accordance with another application, a reactive interface layer can be formed atop the organic semiconductor layer. Chemicals contained in the reactive interface layer are provided to selectively react to a substance in a test medium contacting the exposed surface of the reactive interface layer. A chemical reaction in the reactive interface layer creates a change in charge therein that is detected by a sensor element in the organic semiconductor layer therebelow. This application of the invention is ideally suited for use as an inexpensive, disposable, biochemical sensor, such as a blood glucose sensor.

BRIEF DESCRIPTION OF THE DRAWINGS

FIG. 1 is a schematic cross-section of a sensor element formed in a layer of organic semiconductor material, according to the invention.

FIG. 2 is a schematic cross-section of a sensor element similar to FIG. 1 in which the sensing element senses the lack of an object in contact with its sensing surface.

FIG. 3 is a schematic cross-section similar to FIG. 2 but with an object in contact with the sensing surface of the sensor element showing the sensor element's response thereto.

FIGS. 11–15 are schematic cross-sections showing structures in a sequence of steps in the fabrication of a sensor device that may have an array of sensor cells formed in an organic semiconductor layer.

Figure 4:
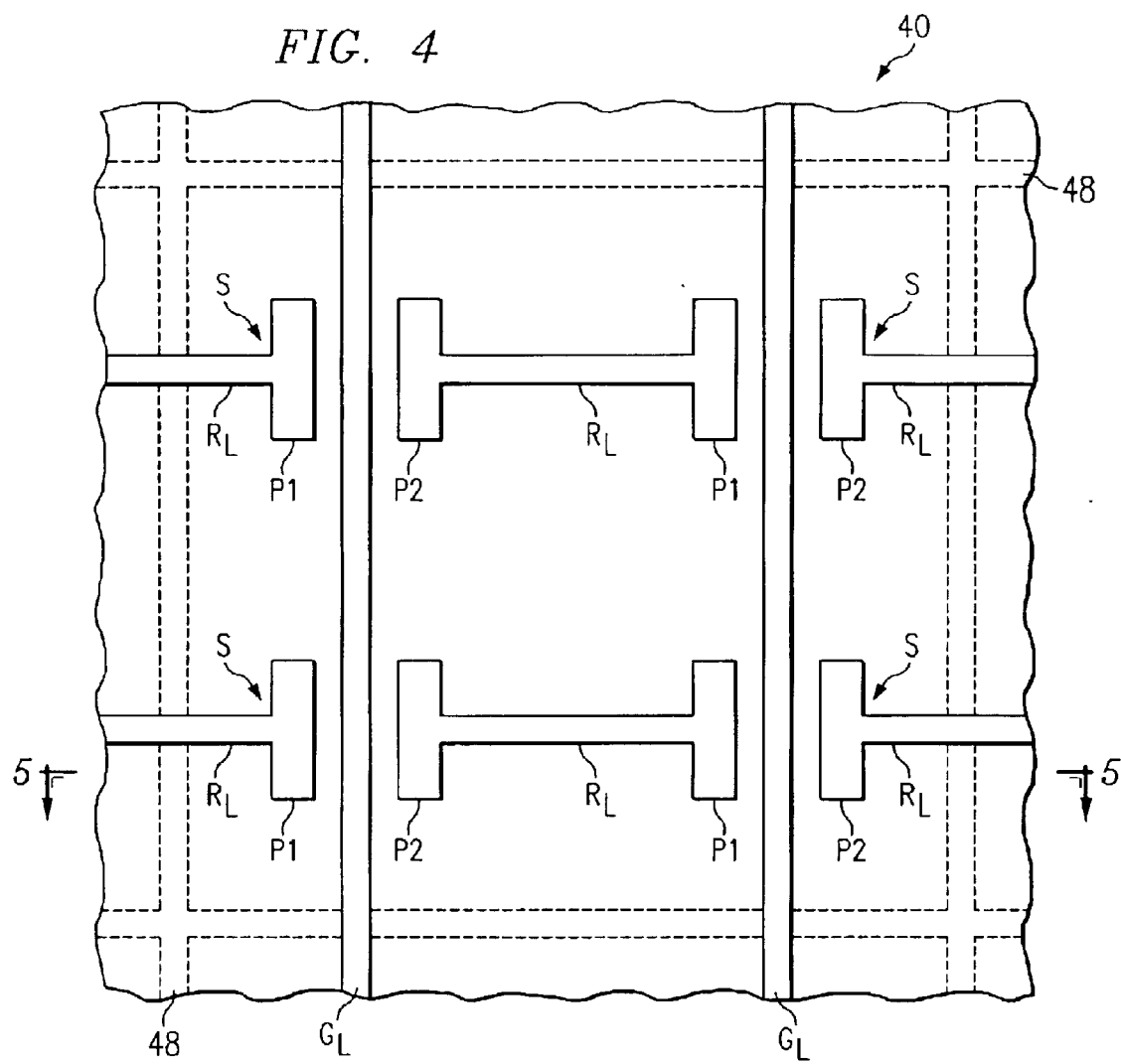
FIG. 4 is a schematic layout in bottom plan view of four sensor elements or cells in a larger array of sensor cells arranged in rows and columns.

The cross-sectional views of the figures are partially cross-hatched. For clarity, cross-hatching has been left off of the organic semiconductor layers, silicon chips and the reactive interface layer in the figures in which they appear.

DETAILED DESCRIPTION OF THE INVENTION

With reference to FIG. 1, a sensor element in accordance with the invention is designated generally by reference numeral 10. The sensor element 10 may have useful applications both as a single such element in a sensing device or as one of many such elements incorporated into an array forming part of a sensor device. The element 10 includes an organic semiconductor layer 12 that can comprise any suitable organic semiconductor material, such as pentacene, that can be prepared with regions of negative and/or positive mobile charges. In its simplest form, the organic semiconductor layer 12 can be chemically structured to provide a uniform distribution of positive majority mobile charge carriers when the layer 12 is in an unbiased state. The sensor element 10 can be constructed from organic semiconductor material having majority mobile charge carriers of either conductivity type. FIG. 1 shows an alternative having a non-uniform distribution of p-type conductivity material in which a relatively thick upper portion 14 extending downward from the upper surface of the organic semiconductor layer 12 has a light concentration of p-type material, and a relatively thin lower portion 16 along the lower surface of the layer 12 that has a heavy concentration of p-type material to enhance conduction between contacts on the lower surface of the layer 12. In the formation of this non-uniform p-type alternative, the layer 12 can comprise a composite of two or more separately formed sublayers bonded together.

The layer 12 has an upper surface defining a sensing surface 18 that comes into contact with an object or fluid to be sensed or comes into close proximity to an object to be sensed without direct contact. In a further alternative of the sensor element 10, a thin insulating film (not shown) can be added atop the sensing surface 18, in which case sensing occurs through the overlying thin insulating film. Conductive plates P1 and P2, which are secured to the bottom surface 20 of the layer 12, serve as contacts for input and output signals applied and sensed at respective terminals 22 and 24. A gate electrode G is also secured to the bottom surface 20 intermediate the conductive plates P1 and P2. The plates P1 and P2 and gate electrode G may comprise a suitable metal, metal alloy, or other conductive material. Silver is a suitable metal. A switch 26, which preferably is implemented as a transistor, provides a means for selectively connecting the gate electrode G to a voltage source 28. In the implementation in which the layer 12 contains positive majority mobile charge carriers, the voltage source 28 is a positive voltage source. It will be appreciated from the description below of various applications of the sensor element 10, that more complex structures are contemplated by the invention in which additional layers and component parts formed from conductive, semiconductor, or insulating material may be added.

The sensor element 10 has two modes of operation. The first mode of operation is a conduction mode in which the gate electrode G is unbiased with switch 26 in its open or OFF condition, thus disconnecting the gate electrode G from the voltage source 28. In this mode, an input signal applied to plate P1 can be communicated through the p-type material near the bottom surface 20 of the layer 12 to the gate electrode G and then through the p-type material again to the plate P2. In an application in which the sensor element 10 is one of many such elements or cells in a two-dimensional array as described below, terminals 22 and 24 can be connected to plates of adjacent sensor cells to provide a conduction path through the interconnected cells. It will be appreciated that the plates P1 and P2 act as capacitor plates as well as drain and source contacts of a junction field-effect transistor (JFET). The JFET is normally fully ON when the gate is unbiased as shown in FIG. 1.

FIGS. 2 and 3 show the sensor element 10 operating in the second of its two modes of operation, which is a sensing mode. In the sensing mode, the switch 26 is in its closed or ON condition causing the gate electrode G to be biased or energized by the positive voltage source 28. The positive voltage bias on the gate electrode G creates a depiction region 30 that extends up into the layer 12, driving the JFET transistor toward its pinch-off condition.

In the example of FIGS. 2 and 3, the sensing element 12 is adapted to sense an object that may be in contact with the sensing surface 18. When the sensing surface 18 is not contacted by such an object as shown in FIG. 2, the positive potential on the gate electrode G creates a depletion region that extends a substantial distance upward into the layer 12. An input signal, such as a square-wave pulse, applied to plate P1 propagates through the undepleted portion of the layer 12 above the gate electrode G to the plate P2 by capacitive coupling. The output signal at plate P2 can be quantified to determine that a small capacitance condition exists in the sensor element 10, thus indicating that an object is not contacting the sensing surface 18.

FIG. 3 shows the sensor element in the sensing mode with an object 32 contacting the sensing surface 18 above the gate electrode G. For example, the object 32 can be a single cell of bacteria. The object 32 modulates the sensor cell capacitance by attracting positive charges into the region of the layer 12 beneath the object causing the height dimension of the depletion region 30 to contract downward towards the gate electrode G. Thus, a relatively large capacitance is sensed at output plate P2 when an input pulse is applied to plate P1 and an object such as object 32 is in contact with the sensing surface 18.

Figure 5:
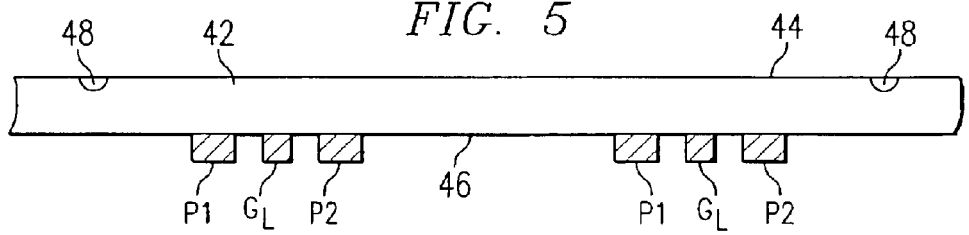
FIG. 5 is a schematic cross-section of a portion of FIG. 4 taken along line 5—5 thereof.

FIGS. 4 and 5 show a portion of a sensor array 40 in which four sensor cells S are shown in two adjacent rows and two adjacent columns running through the array. The array 40 is fabricated in an organic semiconductor layer 42 (shown in cross-section in FIG. 5), which preferably is characterized by a light concentration of p-type conductivity material uniformly distributed throughout the layer 42. An upper planar surface 44 and a lower planar surface 46, which are spaced apart in parallel planes, define the thickness of the layer 42. A substrate (not shown) supports the layer 12 in a manner described below. A pattern of conductors is provided on the lower surface of the organic semiconductor layer 42. At each sensor cell location, the pattern of conductors defines two capacitor plates P1 and P2 with a gate line $G_L$ running vertically between the plates. Row line segments $R_L$ interconnect the sensor cells S in rows so that input signals can be applied to each row and communicated along the row (for example, from left to right), and then sensed at the right-hand extremity of the array 40.

As an optional feature, a grounded surface grid 48 may be provided running periodically through the array 40 between the rows and columns of cells S, preferably implemented by heavily doped p-type lines selectively introduced into the upper surface 44 of the organic semiconductor layer 42. When used as a fingerprint sensor, as described below, the grounded surface grid 48 provides a constant reference voltage at the upper surface 44 to improve the ability to quantify the proximity of the skin of a finger above each of the sensor cells S of the array 40. The grounded surface grid 48 optionally can also be connected to an electrostatic discharge (ESD) protection circuit (not shown).

Figure 6:
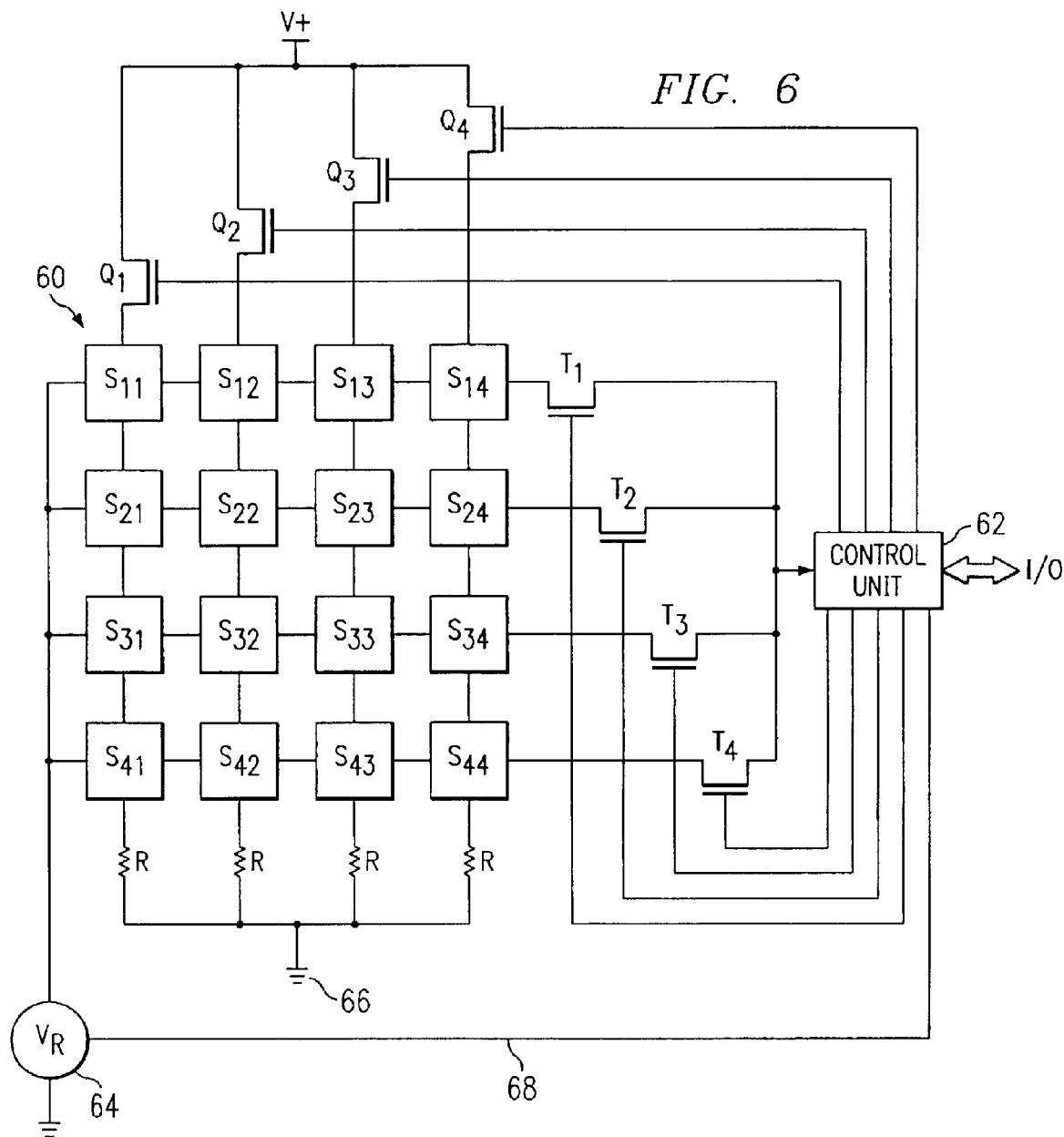
FIG. 6 is a schematic block diagram showing a sixteen-cell sensor array according to an embodiment of the invention.

FIG. 6 shows a sensor array 60 with sixteen sensor cells $S_{11}$ through $S_{44}$ arranged in four rows and four columns. Column select transistors Q1, Q2, Q3, and Q4 selectively energize the columns, one column at a time, under the control of a control unit 62. An input pulse generator 64 sends a pulse signal (such as a square wave pulse) periodically to each of the rows. A line 68 from the control unit 62 to the pulse generator 64 controls the timing of pulses applied to the rows. Row select transistors T1, T2, T3, and T4 selectively interconnect one row at a time with sensing circuitry in the control unit 62, so that the input pulse from generator 64 propagates only through one row at a time. Thus, a single sensor cell can be addressed to determine a capacitance value indicative of an object being sensed above the sensor cell, as previously described. A digital value of the sensed capacitance can be communicated to a system processor (not shown) on a suitable I/O bus from the control unit 62.

When one of the column select transistors $Q_1$, $Q_2$, $Q_3$, or $Q_4$ is turned on, a voltage from a voltage source V+ is applied to that selected column. Load elements R, which may be resistors, cause the selected column to be maintained at a voltage near the positive potential of the voltage source V+. The load elements have a common ground connection 66, causing the non-selected columns to be discharged to ground. Thus, using the sensor cell implementation of FIG. 4 in the array 60 of FIG. 6, the JFET at each cell of a selected column is driven toward pinch-off by the applied voltage V+, while the JFET at each cell of a non-selected column remains in its normally fully ON state.

Figure 7:
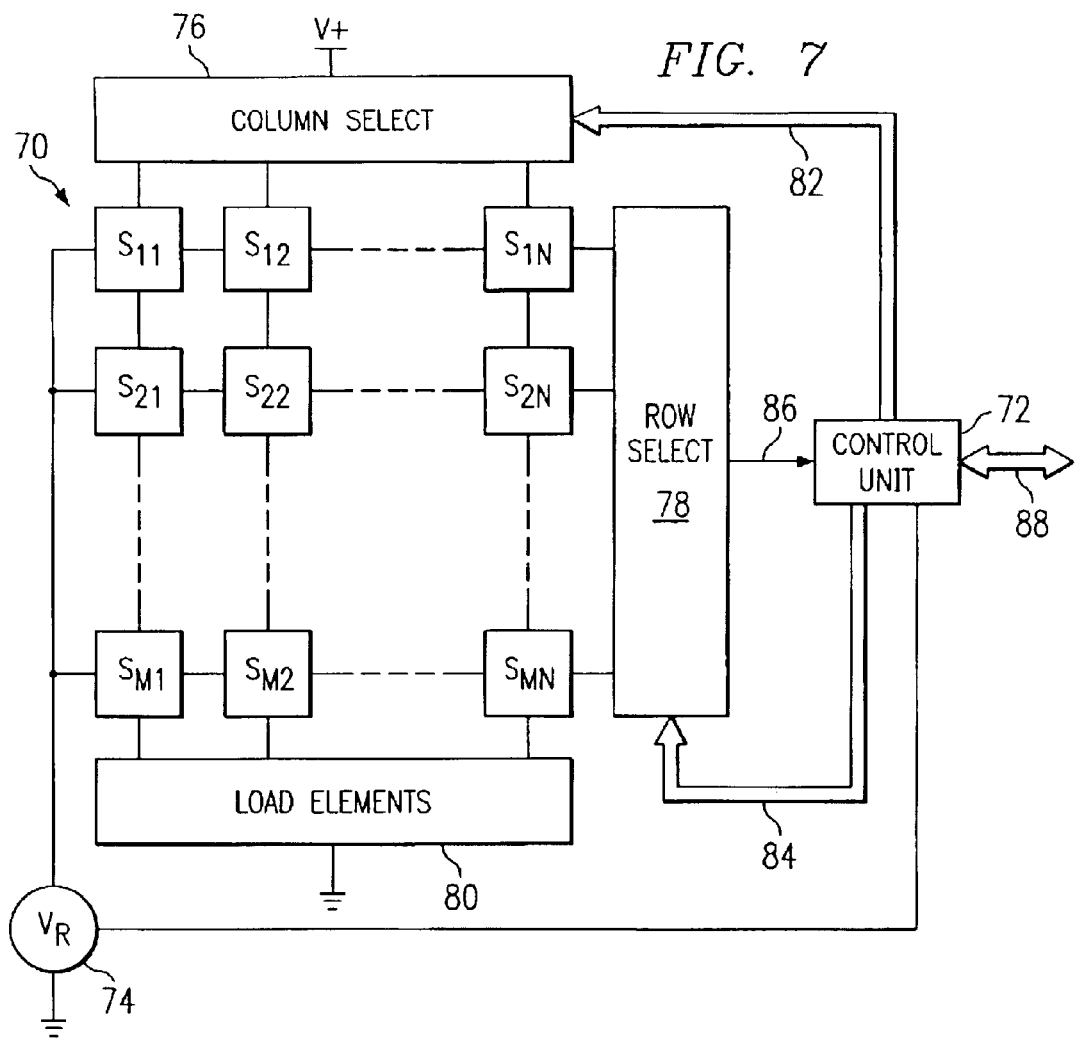
FIG. 7 is a schematic block diagram showing an array of M rows and N columns of sensor cells of a sensor device according to another embodiment of the invention.

FIG. 7 shows an expanded version of the array of FIG. 6. In FIG. 7 there are M rows and N columns to provide a rectangular array 70 of sensor cells $S_{11}$ through $S_{MN}$. In a case where M=N, the array is square. For example, in a fingerprint detector a very large number of sensor cells may be employed in a rectangular or square arrangement. A typical fingerprint sensor array may have 256 by 256 cells, for example. Each cell may occupy a square area that measures between 20 and 100 microns per side.

A control unit 72 controls the operation of the array 70 and a pulse generator 74 that periodically applies input pulse signals to the rows of the array 70. Column select circuitry 76 applies a high voltage potential from a voltage source V+ to one selected column of the array 70 at a time, sequencing through the columns under the control of the control unit 72. Row select circuitry 78 selects one row at a time for sensing the capacitance of the sensor cell corresponding to the selected row and column. Load elements 80 are provided at the bottom of the array 70 to assure that only one selected column at a time is charged to the high voltage potential V+, as described above in connection with FIG. 6.

In a 256-by-256 cell fingerprint detector implemented in accordance with FIG. 7, it is desirable to include address decoder circuitry (not shown) in the column select circuitry 76 and row select circuitry 78 to reduce the number of lines in bus 82 and bus 84 connecting the control unit 72 to the respective select circuitry 76, 78. In particular, eight address lines in each bus 82 and 84 can encode an address of the column and row of a particular cell of the 65,536 cells in the array of 256 by 256 cells. The variable capacitance signal from the selected cell of the array 70 is communicated through the row select circuitry 78 on line 86 to the control unit 72. The control unit 72 may include sensing and amplification circuitry (not shown) that receives the signal on line 86. An amplified output corresponding to the sensed variable capacitance of the selected cell may be converted to a digital output by an analog-to-digital converter (not shown) and then transmitted on input/output bus 88 to a system processor (not shown) for further processing or image generation. Such amplification, A/D conversion, and signal transmission techniques are known in the art of fingerprint detectors.

Figure 8:
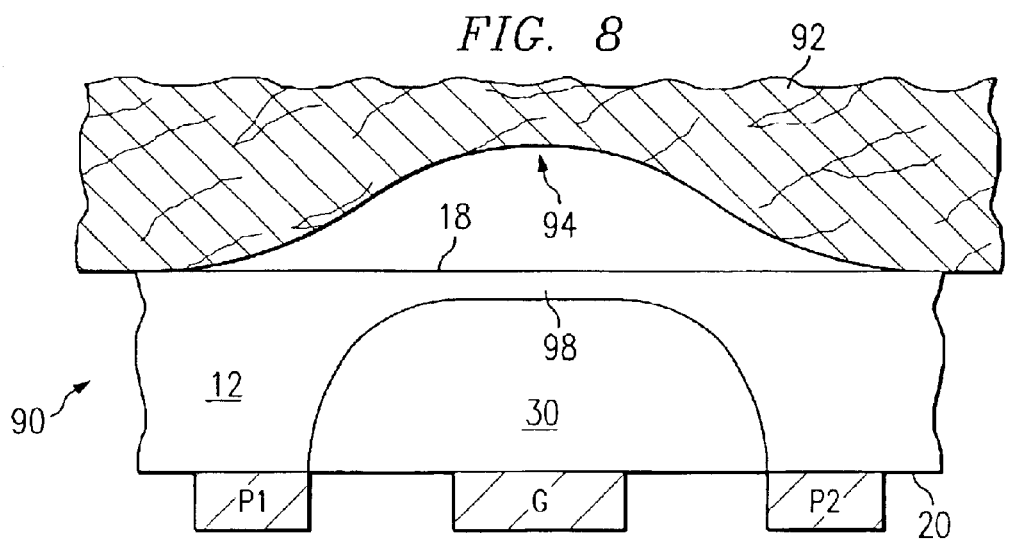
FIG. 8 is a schematic cross-section of a sensor cell of the array of FIG. 7 showing a portion of a human finger in contact with the upper surface of the device with a fingerprint valley above the sensor cell.
Figure 9:
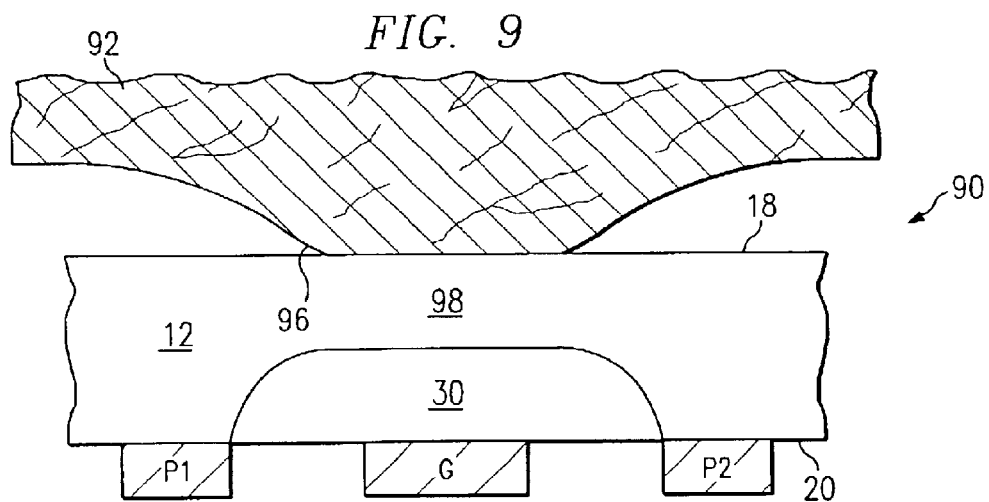
FIG. 9 is a schematic cross-section similar to FIG. 8 but with a fingerprint ridge in contact with the upper surface of the device above the sensor cell.

FIGS. 8 and 9 show the operation of a single sensor element or cell 90 in a fingerprint detector having many such cells in an array. The sensor cell 90 may correspond to the sensor element 10 of FIGS. 1–3 described above, and may be operated in an array like the arrays 40 and 70 of FIGS. 4 and 7. A portion of a finger 92 is shown above the cell 90. In both FIGS. 8 and 9, the gate G is energized with a positive voltage to produce a depletion region 30 in the organic semiconductor layer 12 extending up from the lower surface 20 above the gate G. In FIG. 8, a fingerprint valley 94 appears above the sensor cell 90 so that a JFET channel 98 defined above the depletion region 30 is relatively narrow. In FIG. 9, a fingerprint ridge 96 is in contact with the sensing surface 18 above the sensor cell 90, modulating the depletion region 30 to provide a relatively wide JFET channel 98 between the depletion region and the upper surface 18. The degree of depletion region modulation can be detected by applying a pulse to plate P1 and sensing the transmission of the pulse at plate P2 to determine the capacitance of the JFET channel, a channel with a relatively wide height dimension exhibiting a greater capacitance than a channel with a relatively narrow height dimension. Since only a single column of the sensor array shown in FIG. 7 is energized at a time, the communication of an input pulse along a row provides an output that is a function of the capacitance condition at a single selected sensor cell.

Figure 10:
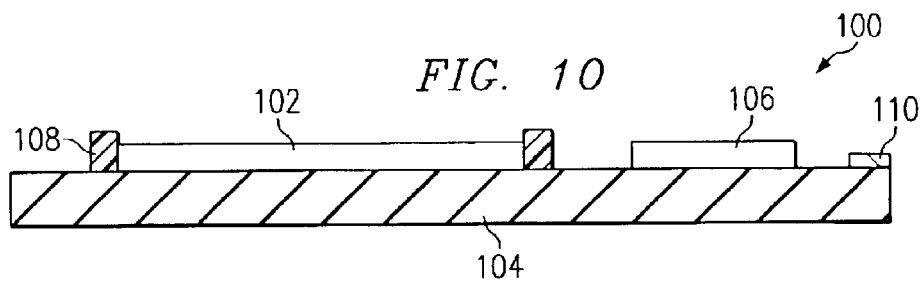
FIG. 10 is a schematic cross-section of a fingerprint sensor device with an organic semiconductor layer for performing the sensing functions and a companion silicon chip for performing the control and communications functions through an interconnect circuit provided by an underlying substrate.

FIG. 10 shows an implementation of a sensor device 100 in which an organic semiconductor layer 102 is mounted on a substrate 104 with a companion silicon chip 106 laterally spaced from the organic semiconductor layer 102. A support frame 108 is used to secure the peripheral edges of the organic semiconductor layer 102 to the substrate 104 and may include connection for the optional grounded surface grid discussed above with reference to FIGS. 4 and 5. The substrate 104 includes an interconnect circuit (not shown) for interconnecting the organic semiconductor layer 102 with the companion silicon chip 106, and with contacts 110 at the periphery of the substrate 104 for communicating I/O signals with a system processor (not shown). Such interconnection techniques are well known in the packaging and PC board arts. The companion silicon chip 106 performs the complex control functions and communicates with the organic semiconductor layer 102, which includes an array of sensor cells, such as the 256-by-256 cell array of FIG. 7. The structure of FIG. 10 may be packaged in a protective housing (not shown), which protects the silicon chip 106 from damage while leaving the upper surface of the organic semiconductor layer 102 exposed to perform its sensing function.

Figure 11:
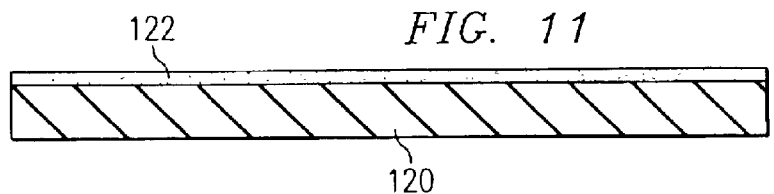
Figure 12:
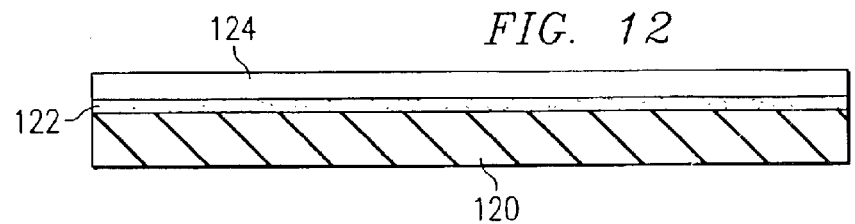

FIGS. 11 through 15 show a sequence of steps for making a sensor device having an array of sensor cells formed in an organic semiconductor layer as previously described. In FIG. 11, a disposable, flexible polymer substrate 120 is provided with a peelable upper surface film 122. Next, as shown in FIG. 12, an organic semiconductor layer 124 is formed atop the peelable film 122, the layer 124 having a major surface contacting the peelable film and an exposed major surface opposite the peelable film. The layer 124 is preferably 20 to 25 microns thick. The peelable film 122 adheres more strongly to the disposable substrate 120 than to the organic semiconductor layer 124. Next, as shown in FIG. 13, a pattern of metal conductors 126 is created atop the organic semiconductor layer 124. This can be accomplished using conventional photolithographic techniques or other suitable coating and printing technologies. Next, as shown in FIG. 14, a permanent substrate 128 with interconnect circuitry is provided, including upper surface contacts 130 for contacting the organic semiconductor layer conductors 126, and metal interconnect lines 132 that may be used to interconnect with a companion silicon chip or an external system processor (not shown). In FIG. 14, the structure of FIG. 13 has been inverted and mounted on the permanent substrate 128 so that conductors of the metal pattern 126 of the organic semiconductor layer 124 are contacted by the contacts 130 on the upper surface of the permanent substrate 128. As shown in FIG. 15, after the structure of FIG. 13 has been inverted and mounted on the permanent substrate 128, the disposable substrate 120 with the peelable film 122 adhered thereto is peeled off of the organic semiconductor layer 124 to expose its sensing surface 134. The structure is then encapsulated or packaged to form the finished sensor device, leaving the sensing surface 134 exposed.

Figure 16:
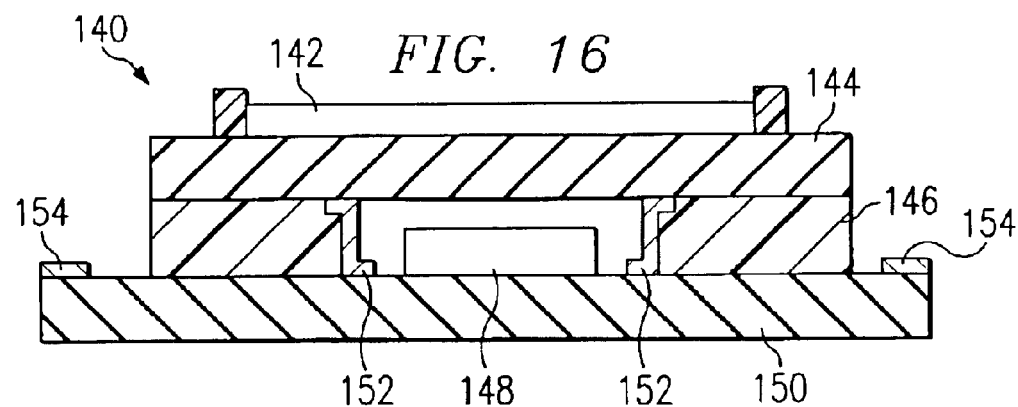
FIG. 16 is a schematic cross-section of a fingerprint sensor device similar to the device of FIG. 10 but with the companion silicon chip mounted beneath the organic semiconductor layer.

FIG. 16 shows a device 140 in an alternative arrangement of the device 100 of FIG. 10 in which the silicon chip is housed beneath the organic semiconductor layer. In FIG. 16, an organic semiconductor layer 142 is mounted on an upper substrate 144, which in turn is mounted on an annular support 146 that includes an interior cavity that contains a companion silicon chip 148. These elements are mounted on a lower substrate 150, such as a PC board. The upper and lower substrates 144 and 150 include conventional interconnect circuitry (not shown). Conductors 152 may be arranged along the interior sidewalls of the annular support 146 to interconnect the upper substrate 144 with the lower substrate 150. Communications with a system processor (not shown) can be made through contacts 154 at the periphery of the lower substrate 150.

As in the embodiment of FIG. 10, the companion silicon chip 148 of the embodiment of FIG. 16 can include all of the addressing, control and sensing circuitry for communicating signals to and from the sensor array that is provided in the organic semiconductor layer 142. For example, the column select circuitry, row select circuitry, load elements, input pulse generator, and control unit shown in FIG. 7 can be included in the silicon chip in either embodiment of FIG. 10 or 16. This simplifies the manufacturing process for making the organic semiconductor layer, which is much larger in area than the area needed for a companion silicon chip that is capable of performing the above-described functions. Compared to conventional silicon-based fingerprint detectors in which the entire sensor array is fabricated in silicon, the use of a small silicon chip as a companion chip with a relatively large organic semiconductor layer that contains the sensor array achieves significant cost savings. In addition, the organic semiconductor layer is more durable than the relatively fragile silicon chips used in prior-art fingerprint detectors. It will be appreciated that the devices of FIGS. 10 and 16 can be repaired by replacing the organic semiconductor layers 102 and 142 in the event that they become damaged, salvaging the more expensive companion silicon chips for continued use.

Figure 17:
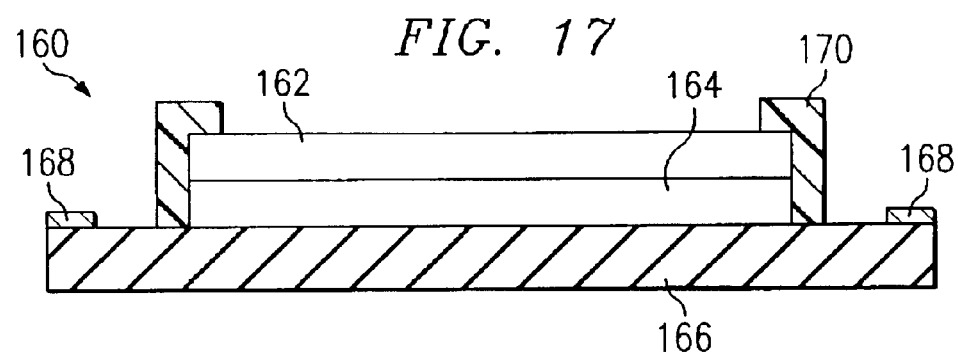
FIG. 17 is a schematic cross-section of a fingerprint sensor device functionally similar to the view of FIG. 16 but replacing the companion silicon chip with a second organic semiconductor layer mounted beneath the upper organic semiconductor layer.

FIG. 17 shows a further alternative embodiment of the present invention in which the sensor device is generally designated by numeral 160. In FIG. 17, two organic semiconductor layers 162 and 164 are included with one mounted atop the other to provide electrical communication therebetween. A sensor cell array as previously described is provided in the upper layer 162. Mounted immediately beneath the upper layer is the lower layer 164 that embodies all of the timing, control, sensing and processor logic of the previously described companion silicon chip. Thus, the fabrication of a more complex organic semiconductor layer is required for the embodiment of FIG. 17 and requires advanced processing techniques in which regions of both negative (n-type) and positive (p-type) charge carriers can be selectively formed in the organic semiconductor layer 164. Additionally, metal interconnect conductors may be provided on the lower surface of the upper layer 162 and on both the upper and lower surfaces of the lower layer 164. The metal interconnect conductors of the lower layer 164 can be interconnected with contacts on the surface of a substrate 166, which also provides system I/O contacts 168 at its periphery. A frame 170 secures the organic semiconductor layers 162 and 164 to the substrate 166.

Figure 18:
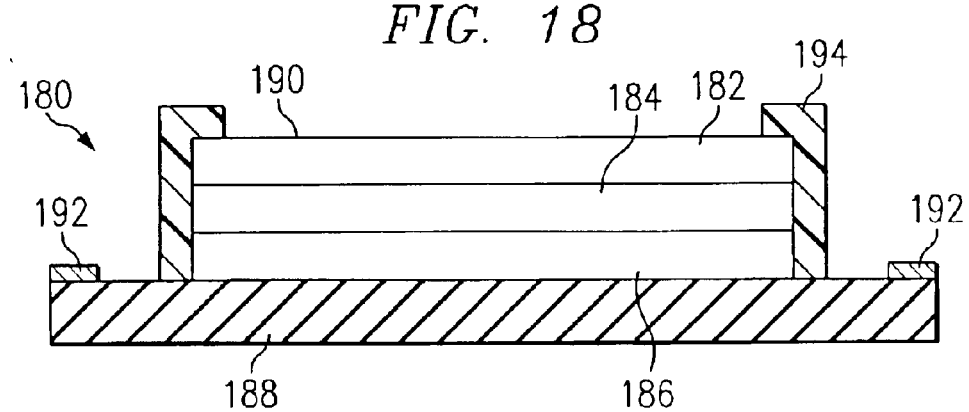
FIG. 18 is a schematic cross-section of another embodiment of a sensor device that includes an upper reactive interface layer for detecting chemical substances coming in contact with its surface.

FIG. 18 shows a further alternative embodiment 180 of the invention in which the embodiment 160 of FIG. 17 has been modified to include a reactive interface layer 182 on the upper surface of an upper organic semiconductor layer 184. In this case, a plurality of sensors, such as the sixteen-cell sensor array of FIG. 6, can be formed in the upper organic semiconductor layer 184 and selectively accessed by a control unit and select transistors similar to that as shown in FIG. 6. Alternatively, a single sensor cell can be provided in the upper layer 184. The control unit and related functions for interacting with the sensor cell or sensor array in layer 184 can be provided in a lower organic semiconductor layer 186. Conductors on the bottom of the lower organic semiconductor layer 186 communicate with contacts on a substrate 188. The reactive interface layer 182 has an upper surface 190 that can be exposed to a test medium (gas or liquid) in contact therewith. The substrate 188 communicates with an external system processor (not shown) through contacts 192 at the periphery of the substrate 188.

The reactive interface layer 182 comprises a polymer that may include a plurality of regions, each region located above a corresponding sensor cell in an array in the upper organic semiconductor layer 184. Each region in the reactive interface layer 182 includes a specific chemical that is contained within the polymer of the layer 182, the specific chemical being selectively reactive to a substance in the test medium contacting the upper surface 190 of the reactive interface layer 182. For example, different enzymes can be provided in selected regions of the reactive interface layer 182. In operation, each enzyme catalyzes a reaction with a specific substance in the test medium. When this reaction occurs, a changed in the charge potential at the isolated region of the reactive interface layer 182 occurs, which can be capacitively sensed by the sensor cell immediately below that particular region of the reactive interface layer. In this manner, the presence of various particular substances can be detected in the test medium.

Alternatively, in the case where a single sensor cell is included in the upper organic semiconductor layer, a single enzyme, such as glucose oxidase, can be provided in the reactive interface layer 182. When the enzyme reacts with a specific substance, such as glucose, in the test medium, a change in charge in the reactive interface layer is sensed by the sensor cell. This embodiment provides a useful biochemical sensor device, such as a blood glucose sensor, that can be disposed of after a single test procedure.

Although preferred embodiments have been described in detail, it should be understood that various changes, substitutions and alterations can be made therein without departing from the spirit and scope of the invention as defined by the appended claims.

What is claimed is:

1. A sensor, comprising:
   an organic semiconductor layer having a sensing surface on one side and a contact surface on the side of the layer opposite from the sensing surface, the layer comprising material having majority mobile charge carriers of a first conductivity type distributed throughout a region beneath the sensing surface;
   a first conductive plate spaced from the sensing surface;
   a second conductive plate spaced from the sensing surface and from the first conductive plate; and
   a gate electrode interposed between the first and second conductive plates, the organic semiconductor layer being so constructed that a depletion region will be formed therein beneath the sensing surface in response to a voltage bias applied to the gate electrode, a dimension of the depletion region varying in response to the presence of an object proximate to the sensing surface, the variation in the dimension being detectable by sensing a signal communicated from the first conductive plate to the second conductive plate through the organic semiconductor layer below the sensing surface;
   wherein the first conductive plate, the second conductive plate, and the gate electrode are each disposed in contact with the contact surface.

2. The sensor of claim 1 wherein the first conductivity type is p-type characterized by a uniform distribution throughout the layer of positive majority mobile charge carriers when the layer is in an unbiased state.

3. A sensor, comprising:
   an organic semiconductor layer having a sensing surface, the layer comprising material having majority mobile charge carriers of a first conductivity type distributed throughout a region beneath the sensing surface;
   a first conductive plate spaced from the sensing surface;
   a second conductive plate spaced from the sensing surface and from the first conductive plate; and
   a gate electrode interposed between the first and second conductive plates, the gate electrode introducing a depletion region in the organic semiconductor layer beneath the sensing surface in response to a voltage bias applied to the gate electrode, a dimension of the depletion region varying in response to the presence of an object proximate to the sensing surface, the variation in the dimension being detectable by sensing a signal communicated through the organic semiconductor layer below the sensing surface;
   wherein the organic semiconductor layer has a non-uniform distribution of p-type conductivity material, the layer including a relatively thick upper portion having a light concentration of p-type material extending downward from the sensing surface and a relatively thin lower portion having a heavy concentration of p-type material extending downward from the relatively thick upper portion to a lower surface of the layer opposite from the sensing surface.

4. An organic semiconductor device, comprising:
   an organic semiconductor layer having upper and lower planar surfaces spaced apart in parallel planes defining the thickness of the layer; and
   a pattern of conductors on the lower surface defining an array of sensor cells arranged in rows and columns, the conductors at each cell location including first and second plates and a gate between the plates, the gate of each cell introducing a depletion region in the organic semiconductor layer in response to a voltage bias applied to all gates of one selected column, the depletion region extending upward from the lower surface, a dimension of the depletion region in the direction perpendicular to the parallel planes varying in response to the presence of an object proximate to the upper surface, the degree of variation of the dimension being detectable by sensing a signal communicated through the organic semiconductor layer below the upper surface of the layer, the signal being communicated through the cells of one selected row, only one cell of the array corresponding to the selected column and selected row being sensed at a time.

5. The organic semiconductor device of claim 4 wherein the organic semiconductor layer comprises p-type conductivity material, characterized by a uniform distribution of positive majority mobile charge carriers above the plates of each sensor cell when the layer is in an unbiased state.

6. The organic semiconductor device of claim 4 further comprising:
   a control unit;
   column select circuitry operating in response to the control unit for connecting only the cells of the selected column to a voltage source to introduce depletion regions above the gates of the cells of the selected column; and
   row select circuitry operating in response to the control unit for connecting only the selected row to the control unit for sensing the signal communicated through the selected row.

7. The organic semiconductor device of claim 6, further comprising:
   a pulse generator connected to the rows operating under the control of the control unit for generating the signal that is communicated through the selected row; and
   a load element for each column connecting the column to a ground connection causing the gates of the cells of the non-selected columns to be discharged to ground while the gates of the cells of the selected column are energized by the voltage source.

8. A fingerprint detector, comprising:
   an organic semiconductor layer having an array of sensor cells formed therein, the layer having an upper sensing surface and conductors on a lower surface;
   a substrate on which the organic semiconductor layer is mounted, the substrate having an upper surface with contacts thereon; and
   a silicon semiconductor chip supported proximate to the organic semiconductor layer and in electrical communication therewith;
   wherein selected contacts on the upper surface of the substrate are connected to the conductors on the lower surface of the organic semiconductor layer;
   wherein the organic semiconductor layer includes a grounded grid disposed therein at the sensing surface; and
   further comprising a frame at the peripheral edges of the organic semiconductor layer for securing the layer to the substrate and providing a connection to the grid.

* * * * *